US00PP36695P2

(12) United States Plant Patent
Grazzini

(10) Patent No.: US PP36,695 P2
(45) Date of Patent: May 20, 2025

(54) ***HIBISCUS* PLANT NAMED 'G21085'**

(50) Latin Name: *Hibiscus moscheutos*
Varietal Denomination: G21085

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 18/933,396

(22) Filed: Oct. 31, 2024

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Hibiscus moscheutos* plant named 'G21085' is disclosed, characterized by large dark red flowers with blue tones, with a distinct dark greyed-purple eye, and minimal venation. Flower size is large, about 7 to 8 inches. Emerging foliage is chocolate brown to violet. Plants are compact, growing to approximately 36 to 42 inches high and wide with dense basal branching. Plants emerge and flower earlier than is typical of the species. The new variety is a *Hibiscus moscheutos*, normally produced as an outdoor garden or container plant.

3 Drawing Sheets

Figure 1:
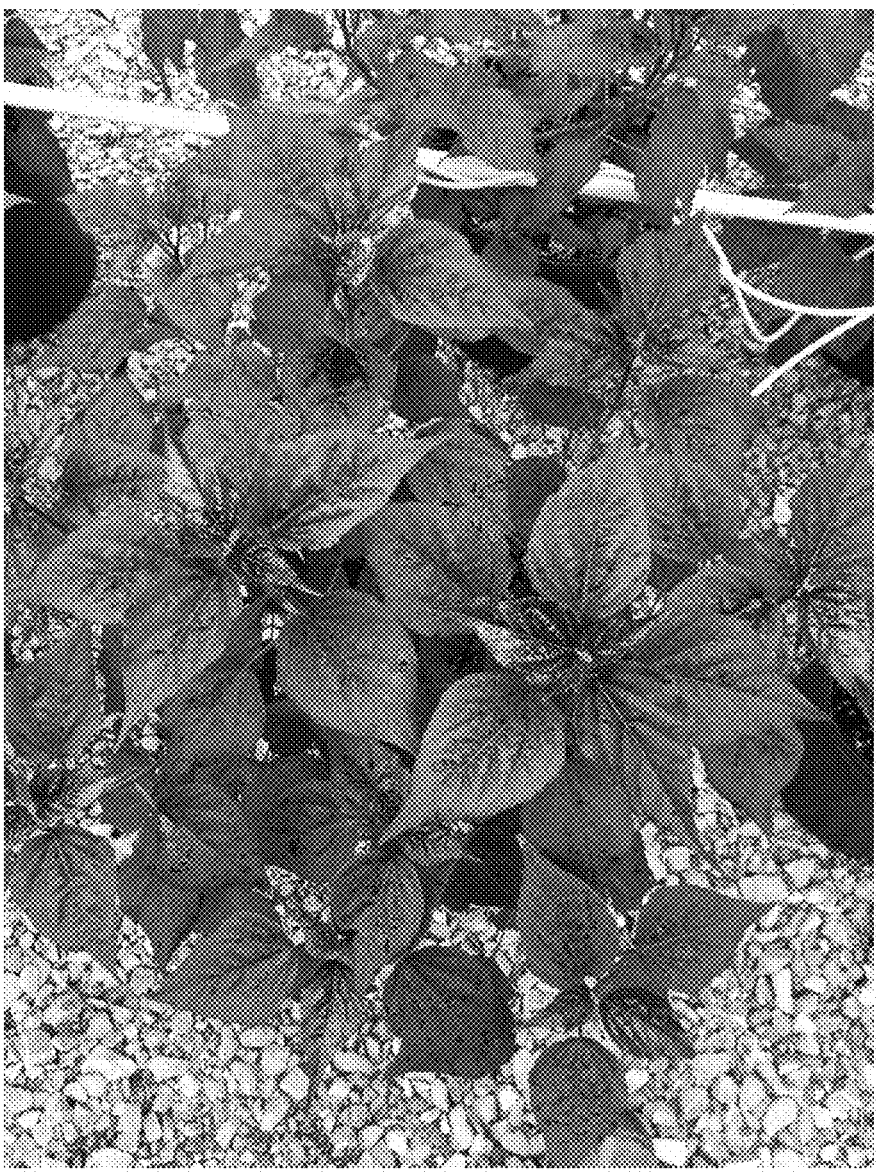

Latin name of the genus and species: *Hibiscus moscheutos*.

Cultivar denomination: 'G21085'.

BACKGROUND OF THE INVENTION

The new cultivar is the product of a planned breeding program conducted by the inventor. The self-pollination resulting in the new cultivar was made between June of 2014 and September of 2015 at a research greenhouse in Bellefonte, Pennsylvania. The parent cultivar is an undistributed, unpatented proprietary cultivar referred to internally as '31857-1'. The new cultivar 'G21085' was derived from self-pollinating '31857-1'. Selection of 'G21085' was made at the same research greenhouse in Bellefonte, PA in August of 2019.

Asexual reproduction of the new cultivar 'G21085' by terminal vegetative cuttings was performed at the same nursery in Bellefonte, Pennsylvania in June of 2020. Subsequent asexual reproduction has shown that the unique features of this cultivar are stable and reproduced true to type through successive generations.

SUMMARY OF THE INVENTION

The cultivar 'G21085' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G21085'. These characteristics in combination distinguish 'G21085' as a new and distinct *Hibiscus* cultivar:

1. 'G21085' has dark red flowers with blue tones, with a large dark greyed-purple eye, and minimal venation. Flower size is large, about 7" to 8" on a well-grown plant.
2. 'G21085' has chocolate brown to dark violet leaves, with slightly fuzzy non-glossy leaf surfaces, above and below.
3. 'G21085' emerges up to a month earlier than typical for the species, and has multiple stems (more than typical) at emergence.
4. 'G21085' flowers early, up to month earlier than typical of the species.
5. 'G21085' has a compact plant habit, 36" to 42" high and wide, and with more dense basal branching than typical.
6. 'G21085' has shown good winter-hardiness, minimum USDA zone 5.

PARENT COMPARISON

Plants of the new cultivar 'G21085' are similar to plants of the parent cultivar, in most horticultural characteristics. However, plants of the new cultivar 'G21085' differ in the following:

1. New cultivar 'G21085' has dark red flowers with blue tones, with a large dark greyed-purple eye. Flowers of the parent variety are light red in color, with a medium red eye.
2. New cultivar 'G21085' has chocolate brown to dark violet leaves, with slightly fuzzy non-glossy leaf surfaces, above and below. The parent variety has densely fuzzy foliage, of a dull brown to chocolate-brown color.
3. New cultivar 'G21085' emerges about 1 week earlier than the parent variety and has fewer stems at emergence than does its parent.

4. New cultivar 'G21085' usually flowers about 1 week earlier than the parent.
5. New cultivar 'G21085' has a compact plant habit, 36" to 42" high and wide, whereas the parent is very compact, typically 30-32" high and wide when grown under the same conditions.

COMMERCIAL COMPARISON

'G21085' can be compared to the commercially known cultivar *Hibiscus* 'Holy Grail', U.S. Plant Pat. No. 31,478. These plants are similar in most horticultural characteristics. However, plants of the new cultivar 'G21085' differ in the following ways:

1. 'G21085' has dark red flowers with blue tones, with a large dark greyed-purple eye, and minimal venation, whereas the comparison variety has dark red flowers with few (if any) blue overtones, and a small red-violet eye. Flower size is comparable, about 7" to 8" in diameter between the new cultivar and this comparator.
2. 'G21085' has chocolate brown to dark violet leaves, with slightly pubescent non-glossy leaf surfaces, above and below. This comparator has darker violet foliage and glossier foliage than the new cultivar.
3. 'G21085' emerges up to a month earlier than this comparator and has more stems at emergence than the comparison cultivar. 'G21085' typically shows 5 to 8 or more shoots at emergence, whereas this comparator typically shows 3 to 5 shoots.
4. 'G21085' flowers up to month earlier than 'Holy Grail' under controlled growing conditions.
5. The new cultivar has a compact plant habit, 36" to 42" high and wide, and with dense basal branching. 'Holy Grail' is both taller and wider than the new variety, typically becoming 48" to 60" tall and wide by the end of the third growing season.

'G21085' can also be compared to the commercially known cultivar *Hibiscus* 'PAS537702', unpatented. These cultivars are similar in most horticultural characteristics. However, plants of the new cultivar 'G21085' differ in the following:

1. 'G21085' has dark red flowers with blue tones, with a large dark violet eye, and minimal venation, whereas this comparator has light red flowers with a small red eye. Flower size of new variety 'G21085' is larger (about 7-8" in diameter) than this comparator (about 5-6" in diameter).
2. 'G21085' has emerging foliage colored chocolate brown to dark violet leaves, with slightly pubescent non-glossy leaf surfaces, above and below. This comparator has emerging foliage colored medium green.
3. New variety 'G21085' emerges up to a month earlier than this comparator when overwintered in-ground or in-container.
4. 'G21085' flowers up to two weeks earlier than this comparator when overwintered in-ground or in-container.
5. 'G21085' has a compact plant habit, 36" to 42" high and wide, and with dense basal branching. This comparator is more compact, about 24" to 30" high and wide.

BRIEF DESCRIPTION OF THE PHOTOGRAPHS

The accompanying photograph in FIG. 1 illustrates a 1-year old plant in Spring with new foliage.

Figure 2:
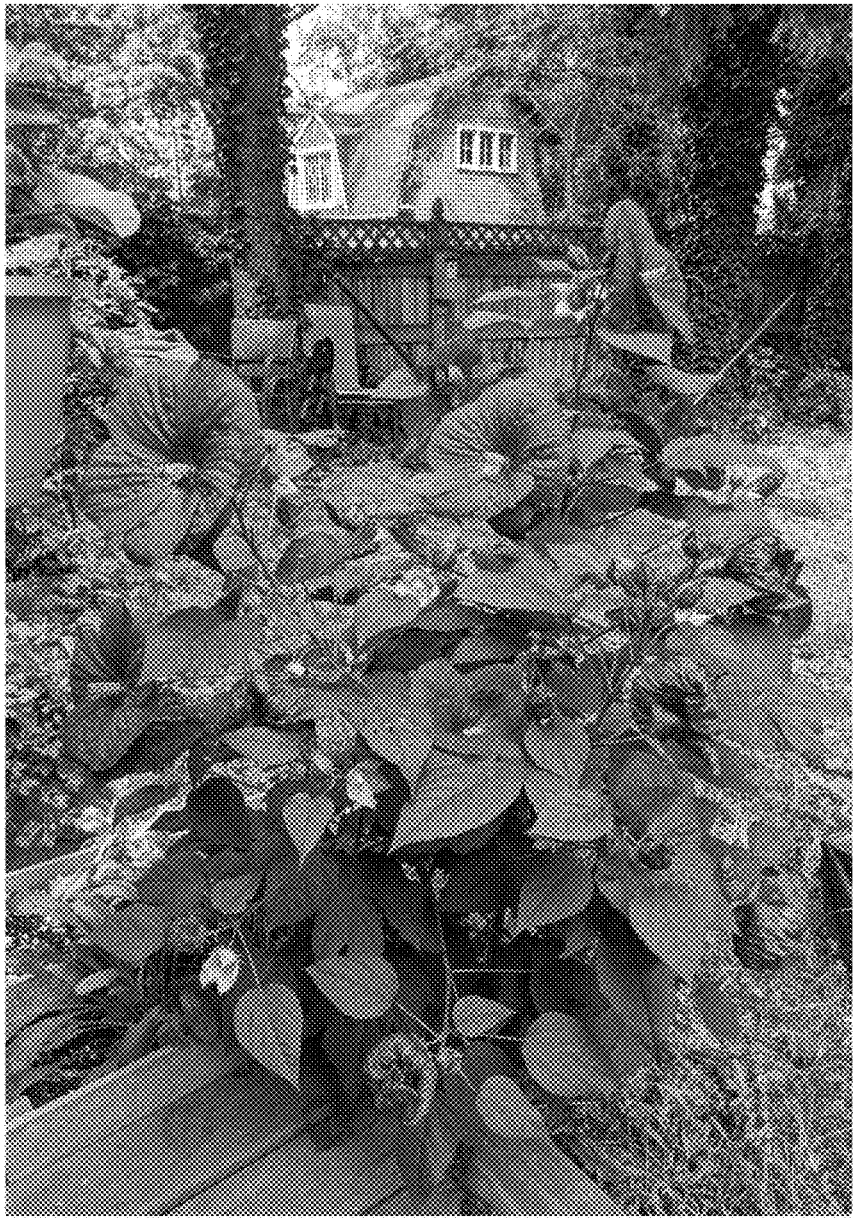

FIG. 2. illustrates a 16-month old flowering plant of 'G21085', during Summer.

Figure 3:
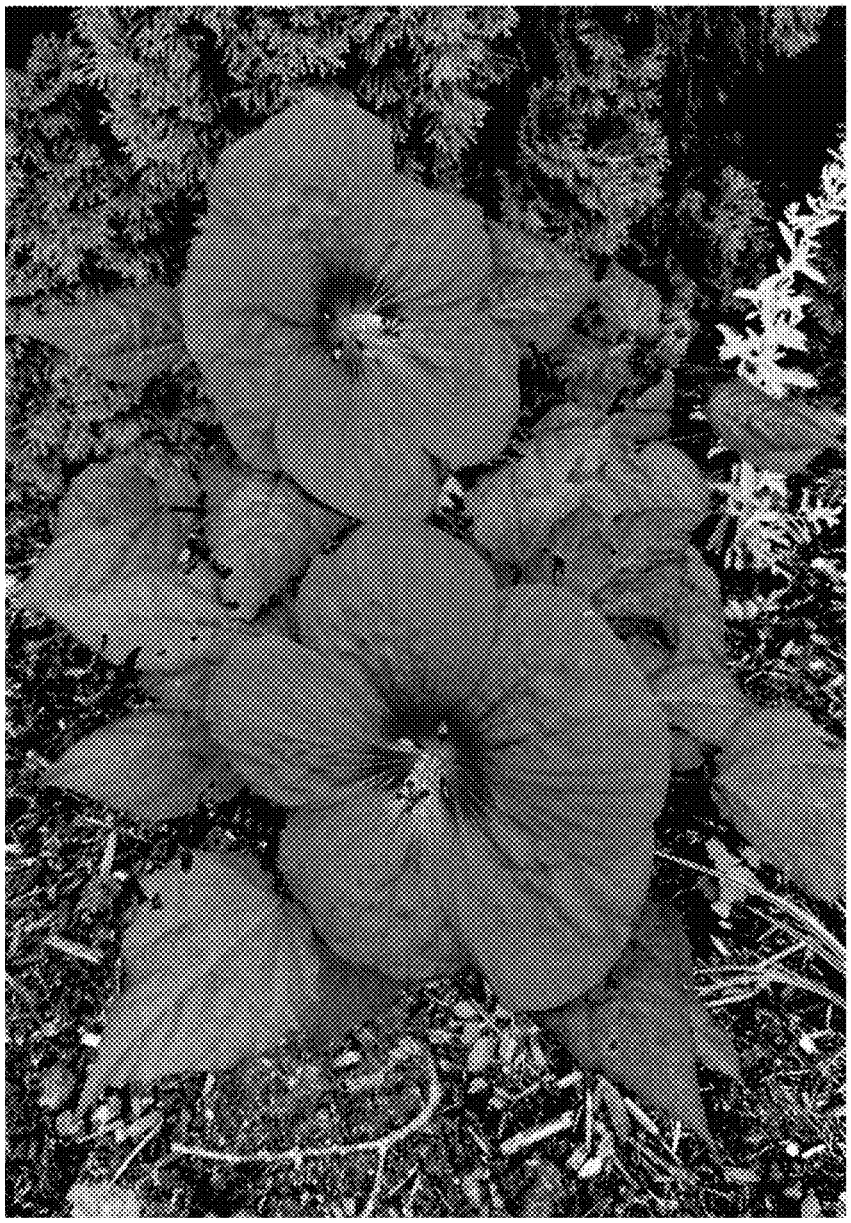

FIG. 3 is a photograph of a 14-month-old flowering plant in early Summer, close-up view of the flowers.

The photographs were taken using conventional techniques and although colors May appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'G21085' plants grown outdoors from Spring to early Summer in Camarillo, California. The growing temperature ranged from about 7° C. to 30° C. during the day and from about 5° C. to 12° C. during the night. General light conditions are bright, normal sunlight. Measurements and numerical values represent averages of typical plant types. Plants are approximately 8 months old from a large rooted cutting. No chemical or photoperiodic treatments were given.

Botanical classification: *Hibiscus moscheutos* 'G21085'.

PROPAGATION

Root description: Woody, moderately well branched. Colored near Brown N200C, N200D and Grey 201B.

PLANT

Growth habit: Upright and somewhat outward. Moderately dense branching and foliage.
Height: Approximately 90 cm to 105 cm.
Plant spread: Approximately 90 cm to 105 cm.
Growth rate: Moderate.
Branching characteristics: Basal and lateral branching.
Length of branches: Approximately 39 to 75 cm.
Diameter branches: Approximately 8 to 12 mm.
Quantity of branches: Approximately 5 to 8 main basal branches.
Texture of lateral branches: Glabrous. Slightly glaucous.
Color of lateral branches:
*Young*.—Near RHS Red-Purple 59C.
*Mature*.—Near RHS Green 137D.
Aspect: Approximately 30° to 60° angle from center of plant.
Strength of Lateral Branches: Very strong.
Internode length: Average range 3.5 to 8 cm.

FOLIAGE

*Arrangement*.—Alternate.
*Average length*.—Average range 9 to 11 cm.
*Average width*.—Average range 5 to 7 cm.
*Shape of blade*.—Ovate.
*Apex*.—Acuminate.
*Base*.—Rounded.
*Attachment*.—Petiolate.
*Margin*.—Irregular serrate.
*Texture of top surface*.—Sparsely pubescent.
*Texture of bottom surface*.—Sparsely pubescent with protruding mid-vein.

*Foliage color*.—Young foliage upper side: Near RHS Greyed-Purple 187A, center vein 185C. Flushed between lateral veins near Purple N79A. Young foliage under side: Near RHS Greyed-Purple 185C, center vein 188B. Overall flush near Purple N79A. Mature foliage upper side: Near RHS Green 139A. Mature foliage under side: Near RHS Green 138A.

*Venation*.—Type: Pinnate. Venation color upper side: Young foliage: Near RHS Greyed-Purple 185C. Mature foliage: Near Red-Purple 59D. Venation color under side: Young foliage: Near RHS Greyed-Purple 185C. Mature foliage: Near Red-Purple 59D.

Petiole:

*Length*.—Average range 5 to 8 cm.
*Diameter*.—Average 4 mm.
*Color*.—Near RHS Green 137D
*Texture*.—Finely pubescent.

INFLORESCENCE

Flower type and habit: Single, rotate, overlapping.
Flower longevity on plant: 2 to 3 days.
Persistence: Self-cleaning.
Fragrance: None.

Bud:

*Shape*.—Ovate.
*Length*.—4.2 cm.
*Diameter*.—2.7 cm at widest.
*Shape*.—Ovate.
*Texture*.—Scabrid.
*Color*.—RHS Green 143D.

Flower size:

*Diameter*.—15 to 20 cm.
*Depth*.—8 cm.

Petals:

*Quantity*.—5.
*Arrangement*.—Rotate. Moderately overlapping.
*Length*.—7 to 11 cm.
*Width*.—6.5 to 8 cm at widest.
*Shape*.—Orbicular to obovate.
*Apex*.—Rounded.
*Base*.—Obtuse.
*Margin*.—Entire.
*Texture, upper and lower surfaces*.—Glabrous, slightly shiny.
*Color*.—Eye — size and feathering: Extends about 10% length of petal from petal base, minimal feathering. When opening, upper surface, main color: Near RHS Red 53A flushed 53C and Blue 103B. When opening, upper surface, eye color: RHS Greyed-Purple 187A. When opening, lower surface: Near RHS Red 53B flushed 53C. Fully opened, upper surface, main color: Near RHS Red 53A flushed 53C and Blue 103A. Fully opened, upper surface, eye color: RHS Greyed-Purple 187A. Fully opened, lower surface: Near RHS Red 53B flushed 53C.

Calyx sepals:

*Quantity*.—5.
*Length*.—3.8 cm.
*Width*.—1.9 cm at widest part.
*Shape* (*overall*).—Deltate. Apex: Acute. Base: Truncate, fused.
*Margin*.—Entire.
*Color*.—Near RHS Green 139C.
*Texture*.—Lightly pubescent.

Epicalyx sepals:

*Quantity*.—5 to 7, typically 6.
*Length*.—2.2 cm.
*Width*.—5 mm at widest part.
*Shape* (*overall*).—Linear-lanceolate, fused at base; campanulate overall.
*Apex*.—Acute.
*Base*.—Truncate.
*Margin*.—Entire.
*Color*.—RHS Green 139B.
*Texture*.—Lightly pubescent.

Peduncle:

*Length*.—Average range 4 to 6 cm.
*Diameter*.—5 mm.
*Angle*.—45° to the lateral branch.
*Strength*.—Moderately strong.
*Texture*.—Slightly pubescent.
*Color*.—RHS Green 139B.

REPRODUCTIVE ORGANS

Stamen stalk:

*Length*.—7.1 cm.
*Diameter*.—6 mm at base, tapering to 4 mm near apex.
*Color*.—Red 46A.
*Protruding beyond petals*.—Very slightly protruding in fully opened flowers.

Stamens:

*Quantity*.—Typically between 40 and 50.

Anthers:

*Shape*.—Globular.
*Length*.—Approximately 2 mm.
*Color*.—RHS Yellow-White 158C
*Pollen*.—Color: RHS Yellow-White 158D Quantity: Sparse.

Pistil:

*Number*.—5.
*Length*.—9 mm.
*Style*.—Length: 5 mm. Color: Near RHS White 155A.
*Stigma*.—Shape: Oblately globular. Color: RHS White 155B. Ovary Color: RHS Green-White 157A.

OTHER CHARACTERISTICS

Disease resistance: Neither resistance nor susceptibility to diseases or pests normal to *Hibiscus* have been observed in this cultivar.

Drought tolerance and temperature tolerance: Hardy perennial, USDA zones 5-9.

Fruit/seed production: Not observed to date.

What is claimed is:

1. A new and distinct cultivar of *Hibiscus moscheutos* plant named 'G21085' as illustrated and described herein.

* * * * *